(12) United States Patent
Lengsfeld et al.

(10) Patent No.: US 11,096,556 B2
(45) Date of Patent: Aug. 24, 2021

(54) DEVICE FOR TESTING THE LEAKPROOFNESS OF A SURGICAL INSTRUMENT, REPROCESSING DEVICE FOR REPROCESSING SURGICAL INSTRUMENTS, AND USE OF A SWELLABLE MATERIAL BODY

(71) Applicant: OLYMPUS WINTER & IBE GMBH, Hamburg (DE)

(72) Inventors: Michael Lengsfeld, Hamburg (DE); Christoph Delzer, Salzhausen (DE); Henning Thate, Hamburg (DE); Benjamin Ottens, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 135 days.

(21) Appl. No.: 16/245,288

(22) Filed: Jan. 11, 2019

(65) Prior Publication Data

US 2019/0142244 A1    May 16, 2019

Related U.S. Application Data

(63) Continuation of application No. PCT/EP2017/066426, filed on Jul. 3, 2017.

(30) Foreign Application Priority Data

Jul. 12, 2016   (DE) .......................... 102016212672.5

(51) Int. Cl.
*A61B 1/00* (2006.01)
*A61B 1/12* (2006.01)
(Continued)

(52) U.S. Cl.
CPC .......... *A61B 1/00057* (2013.01); *A61B 1/123* (2013.01); *A61B 1/125* (2013.01);
(Continued)

(58) Field of Classification Search
CPC ..... A61B 1/123; A61B 1/00057; A61B 90/70; F16K 31/12; G01M 3/042
See application file for complete search history.

(56) References Cited

U.S. PATENT DOCUMENTS 2,718,234 A    9/1955  Blumberg
3,562,731 A *  2/1971  Hsu ....................... G01M 3/045
                                                      340/604
(Continued)

FOREIGN PATENT DOCUMENTS

EP    1906070 A2    4/2008
GB    476845 A      12/1937
(Continued)

OTHER PUBLICATIONS

International Search Report dated Oct. 27, 2017 issued in PCT/EP2017/066426.

*Primary Examiner* — David A. Rogers
(74) *Attorney, Agent, or Firm* — Scully, Scott, Murphy & Presser, P.C.

(57) ABSTRACT

A connecting device through which a gas can flow, for connecting a port of a surgical instrument to a reprocessing device for cleaning the surgical instrument, the connecting device including: a self-actuating valve with a swellable material body.

10 Claims, 2 Drawing Sheets

(51) Int. Cl.
    *G02B 23/24*   (2006.01)
    *G01M 3/04*    (2006.01)
    *G01M 3/28*    (2006.01)
    *F16K 31/00*   (2006.01)

(52) U.S. Cl.
    CPC .......... *F16K 31/001* (2013.01); *G01M 3/042* (2013.01); *G01M 3/2846* (2013.01); *G02B 23/2476* (2013.01)

(56) References Cited

U.S. PATENT DOCUMENTS

| | | | | |
|---|---|---|---|---|
| 4,214,701 A * | 7/1980 | Beckmann | | A01G 25/02 239/63 |
| 4,696,319 A * | 9/1987 | Gant | | A01G 25/167 137/78.3 |
| 4,890,485 A * | 1/1990 | Hsu | | G01M 3/042 210/689 |
| 4,924,860 A * | 5/1990 | Larsen | | B01D 39/00 128/204.21 |
| 5,273,066 A * | 12/1993 | Graham | | A01G 25/167 137/78.3 |
| 5,329,081 A * | 7/1994 | Jones | | A01G 25/167 200/61.04 |
| 5,771,916 A * | 6/1998 | Armenia | | D06F 39/081 137/109 |
| 5,842,346 A * | 12/1998 | Hsu | | F03G 7/06 60/721 |
| 6,412,334 B1 * | 7/2002 | Kral | | A61B 1/00057 73/40 |
| 6,519,941 B1 * | 2/2003 | Sanford | | F42C 3/00 60/721 |
| 6,782,909 B1 * | 8/2004 | Ragless | | G01N 13/04 137/78.3 |
| 8,371,325 B1 * | 2/2013 | Grizzle | | F16K 31/12 137/78.3 |
| 8,550,103 B2 * | 10/2013 | Chen | | E21B 34/08 137/67 |
| 9,968,973 B2 * | 5/2018 | Kosugi | | G08B 21/187 |
| 10,082,505 B2 * | 9/2018 | Melanson | | B01L 3/5027 |
| 10,199,307 B2 * | 2/2019 | Meyer | | F28D 1/0246 |
| 10,702,129 B2 * | 7/2020 | Thate | | G01M 3/2846 |
| 10,729,316 B2 * | 8/2020 | Thate | | A61B 1/00057 |
| 2005/0056081 A1 * | 3/2005 | Gocho | | A61B 1/00057 73/40 |
| 2006/0252991 A1 | 11/2006 | Kubach | | |
| 2007/0161859 A1 * | 7/2007 | Kubach | | H04L 41/0806 600/133 |
| 2007/0169799 A1 * | 7/2007 | Noguchi | | A61B 1/125 134/56 R |
| 2007/0185385 A1 * | 8/2007 | Noguchi | | A61B 1/123 600/132 |
| 2007/0238923 A1 * | 10/2007 | Kubach | | G01M 3/26 600/118 |
| 2009/0220386 A1 * | 9/2009 | Ferri | | C08L 1/286 422/400 |
| 2010/0096119 A1 * | 4/2010 | Sevre | | E21B 43/04 166/51 |
| 2010/0108148 A1 * | 5/2010 | Chen | | F16K 31/001 137/2 |
| 2011/0172615 A2 * | 7/2011 | Greener | | A61F 13/0206 604/319 |
| 2012/0076708 A1 * | 3/2012 | Ferri | | C08L 1/02 422/513 |
| 2012/0160520 A1 * | 6/2012 | Lumbye | | E21B 34/085 166/386 |
| 2012/0160524 A1 * | 6/2012 | Lumbye | | E21B 33/1208 166/387 |
| 2013/0008233 A1 * | 1/2013 | Kosugi | | A61B 1/00059 73/40.5 R |
| 2013/0161411 A1 * | 6/2013 | Grizzle | | F16K 31/12 239/63 |
| 2013/0197309 A1 * | 8/2013 | Sakata | | A61B 1/00114 600/132 |
| 2014/0134071 A1 * | 5/2014 | Suzuki | | A61B 1/123 422/296 |
| 2015/0216608 A1 | 8/2015 | Eschborn et al. | | |
| 2015/0306264 A1 * | 10/2015 | Fabbri | | A61L 2/20 422/292 |
| 2017/0007357 A1 * | 1/2017 | Ottens | | B08B 3/04 |
| 2017/0020367 A1 * | 1/2017 | Tomita | | A61B 1/00 |

FOREIGN PATENT DOCUMENTS

| | | | |
|---|---|---|---|
| JP | 2009-072437 A | 4/2009 | |
| WO | WO-8700439 A1 * | 1/1987 | .......... A61M 1/0052 |
| WO | WO 2015/180951 A1 | 12/2015 | |

* cited by examiner

DEVICE FOR TESTING THE LEAKPROOFNESS OF A SURGICAL INSTRUMENT, REPROCESSING DEVICE FOR REPROCESSING SURGICAL INSTRUMENTS, AND USE OF A SWELLABLE MATERIAL BODY

CROSS-REFERENCE TO RELATED APPLICATION

The present application is a continuation of PCT/EP2017/066426 filed on Jul. 3, 2017, which is based upon and claims the benefit to DE 10 2016 212 672.5 filed on Jul. 12, 2016, the entire contents of each of which are incorporated herein by reference.

BACKGROUND

Field

The present disclosure relates to a device for testing the leakproofness of a surgical instrument, such as an endoscope, with a connecting device, such as through which air can flow, for connecting the device to a port of a surgical instrument.

Furthermore, the present disclosure relates to a reprocessing device for reprocessing surgical instruments, such as endoscopes. Moreover, the present disclosure relates to a use of a swellable material body.

Prior Art

To reprocess surgical instruments, such as flexible endoscopes, normally cleaning and disinfecting devices (RDG-E) are used that are based on a chemical and thermal reprocessing procedure. In order for the endoscope to not be damaged by the cleaning liquid, it is important for the sleeve of the endoscope to be completely intact so that cleaning liquid cannot penetrate into the interior of the endoscope. This is checked in the RDG-E before the first inflow of water by pumping the endoscope up to an excess pressure via a corresponding interface. Then the drop in pressure is monitored, wherein leakage in the endoscope can be deduced from a drop in pressure. If the test fails, or respectively at the end of the procedure, i.e., at the end of the cleaning and disinfecting procedure, the endoscope is again partially ventilated. Reprocessing itself occurs when there is slight excess pressure in the endoscope.

Corresponding RDG-E systems by OLYMPUS Winter & Ibe GmbH, Hamburg, are known by the designation "ETD". These systems comprise a so-called "leak tester" that performs the leakproofness test. In so doing, an endoscope is initially pumped up to an excess pressure of for example 285 mbar relative to the ambient pressure after the start of the program for the leakproofness test, and the excess pressure is reduced after the leakproofness test to about 150 mbar above the ambient pressure. This pressure is maintained during reprocessing and monitored continuously, including to prevent the penetration of water from the outside.

When using the endoscope in endoscopy, damage occasionally occurs in which the endoscope is punctured by biopsy channels. A microperforation arises that in certain circumstances is indiscernible in a performed leakproofness test. During subsequent reprocessing, rinsing and clear water at a much greater pressure than 150 mbar is conducted through the channels to be rinsed. Water from rinsing the channels can thus be transferred into the region of the endoscope to be protected, which causes an increase in pressure in the endoscope above 150 mbar. The leak tester reacts to this by releasing compressed air from the endoscope to maintain the excess pressure of 150 mbar. Water can thus penetrate the tubing by way of the ventilation and ultimately enter the leak tester and, in the worst case, destroy it.

When checking the leakproofness of surgical instruments, such as endoscopes, the endoscope is connected to a leakproofness testing device in order to check whether the outer sleeve of the endoscope and the channels of the endoscope are completely intact.

Before the initial cleaning process with a liquid such as water, a check is automatically performed by connecting the leakproofness testing device to the endoscope via a corresponding port, and then pumping the endoscope up to an over-pressure. Then the drop in pressure is monitored in order to identify leakage in the endoscope.

Due to the interface that for example flexible endoscopes have for checking the leakproofness of the endoscope sleeve and ventilating the endoscope, there is the risk of water penetrating the intact endoscope sleeve from improper handling by a user. Moreover, leaks can arise in the endoscope channels that are not discerned at the low test pressure in the context of the leakproofness test (about 300 mbar); however, at the higher rinsing pressures (about 1300 mbar), they allow water to penetrate into the endoscope sleeve, whereby the excess pressure in the endoscope sleeve (approximately 150 mbar) also cannot be prevented. This can cause the endoscope to be damaged.

To the extent that there is water in a leaky endoscope, this can cause the penetrated water to be able to enter into the cleaning and disinfecting device (RDG-E) during ventilation, which also damages it.

SUMMARY

It is therefore an object to improve testing of leakproofness of surgical instruments, such as endoscopes, in an easy and, if applicable, economical way.

Such object can be achieved by a device for testing the leakproofness of a surgical instrument, such as an endoscope, with a connecting device, such as through which air can flow, for connecting the device to a port of a surgical instrument. The connecting device can have a self-actuating valve with a swellable material body.

In a leakproofness testing device for a surgical instrument, air can flow through the connecting device when ventilating the instrument, wherein the connecting device connects the leakproofness testing device and an endoscope to each other. In this case, a self-actuating valve is arranged in the connecting device through which air can flow, wherein it is discerned whether water is in the air flow from the surgical instrument by means of the material body in the connecting device that can swell with water. The material body can swell hygroscopically from contact with water in the outflowing air from the surgical instrument, whereby the channel of the connecting device is plugged, or respectively blocked by means of the swollen material body due to the contact with water, whereby the air flow through the connecting device is interrupted.

Since the presence of water in the air flow is easily discerned by means of the swellable material body and since the channel in the connecting device is blocked after the material body swells, this prevents water that has secretly penetrated into the surgical instrument from migrating into the cleaning and disinfecting device, whereby the cleaning and disinfecting device as well as further endoscopes are not thereby damaged.

It is furthermore envisioned in this regard that the swellable material body is configured to swell upon contact with a liquid, such as water, and to block the flow of air, such as when ventilating, through the connecting device. This yields a valve function, wherein the material body is made to swell when the material body contacts water from the endoscope, and this blocks the connecting device in the flow direction of the air flow while ventilation.

The connecting device can be configured in this regard with a channel through which air can flow, wherein the swellable material body is arranged in the channel. In this case, the material body can be arranged in the channel so as to be exchangeable.

According to an embodiment, with regard to the device, it is provided that the swellable material body is hygroscopic, and/or that the swellable material body is made of cellulose, such as fiber-reinforced cellulose, and/or that the swellable material body is configured as a swellable membrane body.

The material body can be designed as a swelling disk in an embodiment.

The swellable material body can be arranged in a housing through which air can flow with an air inlet side and an air outlet side.

Furthermore, a sieve can be arranged at the air inlet side of the housing, and/or a sieve can be arranged at the air outlet side of the housing, wherein the material body is arranged between the air inlet side and the air outlet side. By using sieves at the air inlet side and the air outlet side, the swellable material body can be restricted, wherein the material body is kept compact by the sieves, and a release of the material from the swellable material body is prevented.

Moreover, an embodiment of the device provides that the connecting device can be configured as a connecting line, such as a ventilation line, or as an adapter. In this context, the connecting line can be provided with a swellable material body, such as a swelling disk. Moreover, as an alternative, the swellable material body can be arranged in the adapter provided with a channel.

Furthermore, in an embodiment of the device the connecting device can have a liquid sensor, such as a water sensor, which increases the discernment of water in the surgical instrument tested, or respectively to be tested.

It is moreover provided that the liquid sensor can be arranged at the inlet side before the swellable material body relative to the flow direction of air through the connecting device when ventilating. By means of the liquid sensor, the resistance of the air, or respectively the circular medium, can be monitored. If the resistance decreases from contact with water from the air, a signal is triggered so that it can be determined that the connecting device is blocked due to the material body being swollen by water.

Moreover, such object can be achieved by a reprocessing device for reprocessing surgical instruments, such as endoscopes, with a device for testing the leakproofness of a surgical instrument as described above. We expressly refer to the above explanations in order to avoid repetitions.

Furthermore, by using a swellable material body in a device for testing the leakproofness of a surgical instrument, such as an endoscope as described above. In this regard, reference is also expressly made to the above statements.

Further features will become apparent from the description of embodiments together with the claims and the included drawings. Embodiments can fulfill individual characteristics or a combination of several characteristics.

BRIEF DESCRIPTION OF THE DRAWINGS

The embodiments are described below, without restricting the general idea of the invention, using exemplary embodiments with reference to the drawings, whereby we expressly refer to the drawings with regard to all details that are not explained in greater detail in the text. In the figures.

In the drawings, the same or similar elements and/or parts are each provided with the same reference numbers in order to prevent each item from needing to be reintroduced.

DETAILED DESCRIPTION

Figure 1:
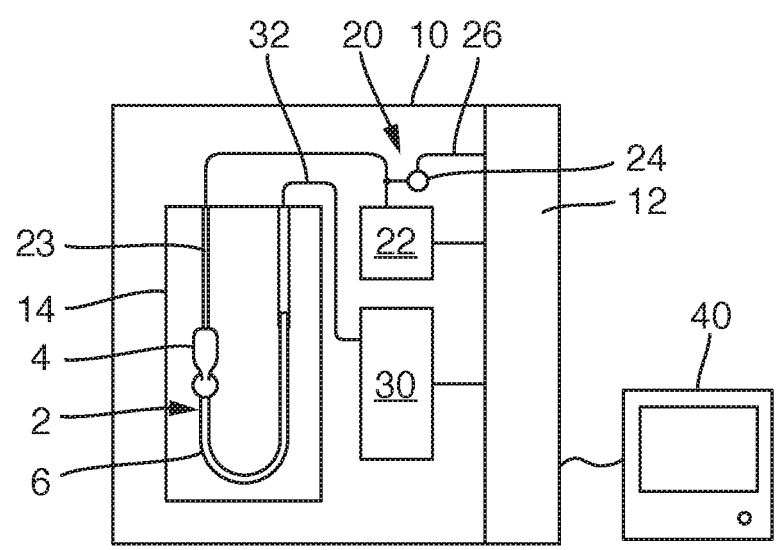
FIG. 1 illustrates a schematic representation of a cleaning and disinfecting device.

FIG. 1 shows a schematic representation of a reprocessing system 10, in the cleaning chamber 14 of which a flexible endoscope 2 is arranged that is ready to be cleaned and disinfected. The endoscope 2 comprises a handle 4 as well as a flexible shaft 6 which are both connected to connections of the reprocessing system 10.

The shaft 6 of the endoscope 2 is connected by a port to a reprocessing apparatus 30 of the reprocessing system 10, whereas the handle 4 is connected by a compressed air hose 23 with a compressed air source 22, such as a compressor, to the device 20 for supplying compressed air, termed a "leakage tester" for short. Like the reprocessing apparatus 30, this is connected to a control apparatus 12 of the reprocessing system 10 which accordingly also represents a control apparatus for the apparatus 20 for applying compressed air.

At the outlet of the compressed air source 22, an air pressure sensor 24 is connected to the compressed air hose 23 that measures the excess pressure of the air in the compressed air hose 23 above the ambient pressure, and also transmits corresponding signals via a signal line 26 to the control apparatus 12 of the reprocessing system 10. The control apparatus 12 is moreover connected to a display apparatus 40 by means of which the control apparatus 12 can be influenced externally, and conversely, data from the control apparatus 12 can be displayed, such as excess pressure measured data from the air pressure sensor 24 and/or process data.

The apparatus 20 for applying compressed air is connected from a compressed air source 22 via a compressed air hose 23 to an endoscope 2, which is only schematically indicated, wherein compressed air is pumped into the endoscope 2 and then also released.

An air pressure sensor 24 is connected to the compressed air hose 23 and measures the pressure of the air pressure in the compressed air hose 23 and in the endoscope 2. The air pressure sensor 24 can alternatively also measure directly at the endoscope 2 or at the outlet of the compressed air source 22.

Figure 2:
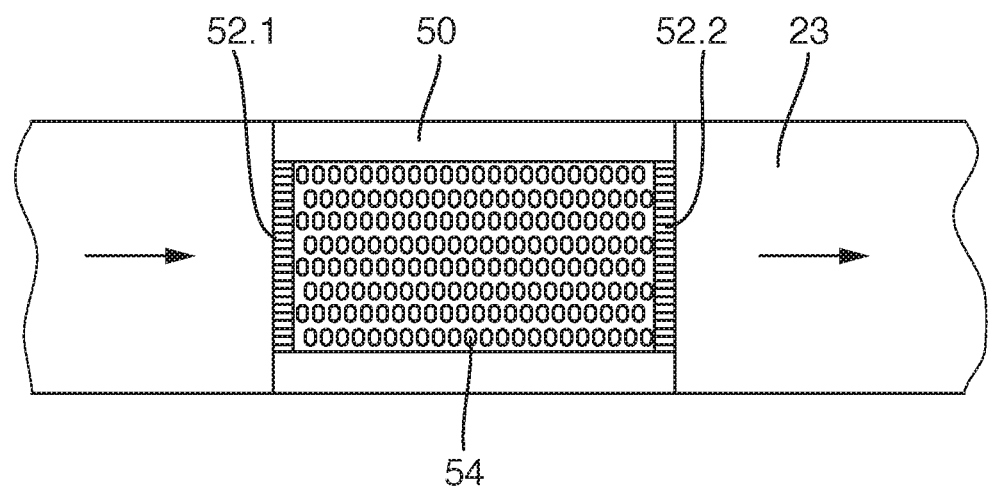
FIG. 2 illustrates a cross-section of a compressed air hose for connecting a compressed air source to an endoscope, and FIG. 3 schematically illustrates a cross-section of a compressed air hose according to another embodiment.
Figure 3:
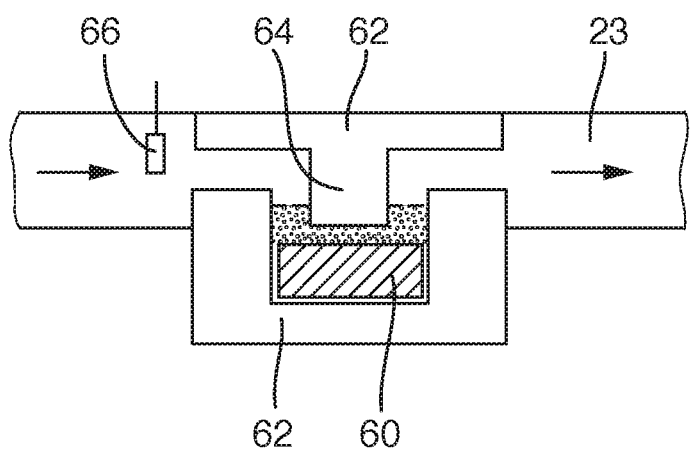

Cross-sections of different embodiments of a compressed air hose 23 are shown in FIGS. 2 and 3.

With the compressed air hose 23 shown in FIG. 2, a cartridge 50 is arranged in the compressed air hose 23 that has a sieve 52.1 and a sieve 52.2 on both sides to let an air flow pass through. When performing the leakproofness test of the endoscope while releasing air pumped into the endoscope, the sieve 52.1 is arranged at the air inlet side, and the sieve 52.2 is arranged at the air outlet side. A swelling material, or respectively a swellable material body 54 is arranged between the sieves 52.1, 52.2 and lets air from the endoscope pass through when dry air flows through, or respectively when releasing the air.

When the swelling material 54 contacts water in the air flow, the material body 54 swells and blocks the compressed air hose 23 such that the air flow is interrupted and blocked. This yields a complete blockage, or respectively stoppage in the compressed air hose 23 from the swelling of the swelling body 54. Contamination of other endoscopes with water when subsequently cleaning a plurality of endoscopes in the reprocessing system is thereby avoided. After the swelling material, or respectively the material body 54, contacts water, the cartridge 50 in the compressed air hose 23 is exchanged.

Instead of the swellable material body 54, the cartridge 50 can thus also have swellable membrane material, or respectively a swellable membrane that swells upon contact with water and also causes a blockage of the air flow in the compressed air hose 23.

In the exemplary embodiment shown in FIG. 3, a swelling disk 60 is arranged in a pot-shaped recess in a valve body 62. When ventilating the endoscope and checking the leakproofness, the air flow is meanderingly guided through the valve body 62 in which the swelling disk 60 is arranged. If the air flow guided through the valve body 62 contains water, the swelling disk 60 swells and comes in contact with a projection 64 of the valve body 62 such that the swelling disk surrounds the projection 64 in a swollen state and interrupts the air flow. This interrupts the free flow path of the volumetric flow while ventilating, and interrupts the outlet side of the valve body 62 from the inlet side for the air flow. The swollen state of the swelling disk 60 is portrayed in a dashed line.

In another embodiment, a water sensor 66 can additionally, or respectively optionally be arranged at the inlet side of the air flow, by means of which it is additionally discerned whether water is in the ventilating air flow. In the reprocessing device, it can thereby be additionally discerned that the swelling disk 60 has swollen from water in the endoscope.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
4 Handle
6 Flexible shaft
10 Reprocessing system
12 Control unit
14 Cleaning chamber
20 Apparatus for applying compressed air
22 Compressed air source
23 Compressed air hose
24 Air pressure sensor
26 Signal line
30 Reprocessing apparatus
32 Rinsing hose
40 Display unit
50 Cartridge
52.1, 52.2 Sieve
54 Material body
60 Swelling disk
62 Valve body
64 Projection
66 Water sensor

The invention claimed is:

1. A reprocessing device for cleaning a surgical instrument, the reprocessing device comprising:
   a connecting device through which a compressed gas can flow, for connecting a port of the surgical instrument to the reprocessing device for cleaning the surgical instrument, the connecting device comprising:
      a compressed gas hose for connection to the port of the surgical instrument, the compressed gas hose being configured to provide the compressed gas to the port of the surgical instrument through an internal conduit;
      wherein the compressed gas hose having a self-actuating valve with a swellable material body disposed in the internal conduit;
      wherein the self-actuating valve comprises a replaceable cartridge through which the compressed gas can flow from an inlet side to an outlet side of the self-actuating valve;
      the cartridge having a first sieve arranged at the inlet side of the self-actuating valve, a second sieve arranged at the outlet side of the self-actuating valve, and the swellable material body being arranged between the first sieve and the second sieve; and
      the swellable material body is configured to swell upon contact with a liquid and, when swelled, to block the flow of the compressed gas to the outlet side of the self-actuating valve.

2. The reprocessing device according to claim 1, wherein the swellable material body is one or more of a hygroscopic material body, a cellulose material body, a fiber-reinforced cellulose material body, and a swellable membrane body.

3. The reprocessing device according to claim 1, further comprising a liquid sensor in communication with the compressed gas flow.

4. The reprocessing device according to claim 3, wherein the liquid sensor is a water sensor.

5. The reprocessing device according to claim 3, wherein the liquid sensor is arranged at an inlet side of the self-actuated valve before the swellable material body relative to a flow direction of the compressed gas.

6. A reprocessing device for cleaning a surgical instrument, the reprocessing device comprising:
   a connecting device through which a compressed gas can flow, for connecting a port of the surgical instrument to the reprocessing device for cleaning the surgical instrument, the connecting device comprising:
      a compressed gas hose for connection to the port of the surgical instrument, the compressed gas hose being configured to provide the compressed gas to the port of the surgical instrument through an internal conduit;
      wherein the compressed gas hose having a self-actuating valve, the self-actuating valve comprises:
         a projection partially disposed in a flow path of the compressed gas through the self-actuating valve between an inlet side and an outlet side of the self-actuating valve;

a recess disposed so as to oppose the projection; and a swellable material body disposed in the recess, the swellable material body being configured to swell upon contact with a liquid and, when swelled, engages the projection to block the flow of the compressed gas to the outlet side of the self-actuating valve.

7. The reprocessing device according to claim 6, wherein the swellable material body is one or more of a hygroscopic material body, a cellulose material body, a fiber-reinforced cellulose material body, and a swellable membrane body.

8. The reprocessing device according to claim 6, further comprising a liquid sensor in communication with the compressed gas flow.

9. The reprocessing device according to claim 8, wherein the liquid sensor is a water sensor.

10. The reprocessing device according to claim 8, wherein the liquid sensor is arranged at an inlet side of the self-actuated valve before the swellable material body relative to a flow direction of the compressed gas.

* * * * *